United States Patent
Tykocinski

(10) Patent No.: US 9,221,895 B2
(45) Date of Patent: Dec. 29, 2015

(54) OX40/TRAIL FUSION PROTEINS

(75) Inventor: Mark L. Tykocinski, Merion Station, PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 556 days.

(21) Appl. No.: 13/256,401

(22) PCT Filed: Mar. 11, 2010

(86) PCT No.: PCT/US2010/027000
§ 371 (c)(1),
(2), (4) Date: Jan. 26, 2012

(87) PCT Pub. No.: WO2010/105068
PCT Pub. Date: Sep. 16, 2010

(65) Prior Publication Data
US 2012/0121640 A1    May 17, 2012

Related U.S. Application Data

(60) Provisional application No. 61/159,941, filed on Mar. 13, 2009.

(51) Int. Cl.
C07K 14/705    (2006.01)
A61K 38/00     (2006.01)

(52) U.S. Cl.
CPC ..... *C07K 14/70575* (2013.01); *C07K 14/70578* (2013.01); *A61K 38/00* (2013.01); *C07K 2319/00* (2013.01)

(58) Field of Classification Search
None
See application file for complete search history.

(56) References Cited

U.S. PATENT DOCUMENTS

| 6,046,310 | A | 4/2000 | Queen et al. |
| 6,284,236 | B1 * | 9/2001 | Wiley et al. ................. 424/85.1 |
| 7,569,663 | B2 | 8/2009 | Tykocinski et al. |
| 2001/0021516 | A1 | 9/2001 | Wei et al. |
| 2005/0069548 | A1 * | 3/2005 | Hussell et al. ............ 424/178.1 |
| 2005/0158823 | A1 | 7/2005 | Wiley et al. |
| 2007/0297977 | A1 | 12/2007 | Yu et al. |

FOREIGN PATENT DOCUMENTS

WO    WO 2008/120832    10/2008

OTHER PUBLICATIONS

Gerritsen et al., "In silico data filtering to identify new angiogenesis targets from a large in vitro gene profiling data set." 2002, Physiol Genomics 10:13-20.
Razmara et al.,"Fn14-TRAIL, a Chimeric Intercellular Signal Exchanger, Attenuates Experimental Autoimmune encephalomyelitis." 2009, Am J Pathol 174(2):460-474.
Higgins et al., "Regulation of T cell activation in vitro and in vivo by targeting the OX40-OX40 ligand interaction: amelioration of ongoing inflammatory bowel disease with an OX40-IgG fusion protein, but not with an OX40 ligand-IgG fusion protein." 1999, J Immunol 162(1):486-493.
Yellali et al., "A single intrathecal injection of DNA and an asymmetric cationic lipid as lipoplexes ameliorates experimental autoimmune encephalomyelitis." 2011, Mol Pharm 8(5):1980-1984.

* cited by examiner

*Primary Examiner* — Anand Desai
(74) *Attorney, Agent, or Firm* — Riverside Law LLP

(57) ABSTRACT

Fusion proteins which act on the OX40/TRAIL signaling axes are provided. The proteins are useful in the treatment or amelioration of autoimmune diseases, particularly multiple sclerosis, and alloimmune diseases, as well as cancer.

11 Claims, 12 Drawing Sheets

SEQUENCE LISTING

```
<160> NUMBER OF SEQ ID NOS: 10

<210> SEQ ID NO 1
<211> LENGTH: 398
<212> TYPE: PRT
<213> ORGANISM: Homo sapiens

<400> SEQUENCE: 1

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Glu Thr Ile Ser Thr Val Gln Glu Lys Gln
    210                 215                 220

Gln Asn Ile Ser Pro Leu Val Arg Glu Arg Gly Pro Gln Arg Val Ala
225                 230                 235                 240

Ala His Ile Thr Gly Thr Arg Gly Arg Ser Asn Thr Leu Ser Ser Pro
                245                 250                 255

Asn Ser Lys Asn Glu Lys Ala Leu Gly Arg Lys Ile Asn Ser Trp Glu
            260                 265                 270

Ser Ser Arg Ser Gly His Ser Phe Leu Ser Asn Leu His Leu Arg Asn
        275                 280                 285

Gly Glu Leu Val Ile His Glu Lys Gly Phe Tyr Tyr Ile Tyr Ser Gln
```

```
                290                 295                 300
Thr Tyr Phe Arg Phe Gln Glu Ile Lys Glu Asn Thr Lys Asn Asp
305                 310                 315                 320

Lys Gln Met Val Gln Tyr Ile Tyr Lys Tyr Thr Ser Tyr Pro Asp Pro
                325                 330                 335

Ile Leu Leu Met Lys Ser Ala Arg Asn Ser Cys Trp Ser Lys Asp Ala
                340                 345                 350

Glu Tyr Gly Leu Tyr Ser Ile Tyr Gln Gly Gly Ile Phe Glu Leu Lys
                355                 360                 365

Glu Asn Asp Arg Ile Phe Val Ser Val Thr Asn Glu His Leu Ile Asp
                370                 375                 380

Met Asp His Glu Ala Ser Phe Phe Gly Ala Phe Leu Val Gly
385                 390                 395

<210> SEQ ID NO 2
<211> LENGTH: 379
<212> TYPE: PRT
<213> ORGANISM: Homo sapiens

<400> SEQUENCE: 2

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
                115                 120                 125

Pro Pro Gly His Phe Ser Pro Gly Asp Asn Gln Ala Cys Lys Pro Trp
            130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
                180                 185                 190

Glu Ala Trp Pro Arg Thr Ser Gln Gly Pro Ser Thr Arg Pro Val Glu
                195                 200                 205

Val Pro Gly Gly Arg Ala Arg Gly Pro Gln Arg Val Ala Ala His Ile
            210                 215                 220

Thr Gly Thr Arg Gly Arg Ser Asn Thr Leu Ser Ser Pro Asn Ser Lys
225                 230                 235                 240

Asn Glu Lys Ala Leu Gly Arg Lys Ile Asn Ser Trp Glu Ser Ser Arg
                245                 250                 255

Ser Gly His Ser Phe Leu Ser Asn Leu His Leu Arg Asn Gly Glu Leu
                260                 265                 270
```

-continued

```
Val Ile His Glu Lys Gly Phe Tyr Ile Tyr Ser Gln Thr Tyr Phe
            275                 280                 285

Arg Phe Gln Glu Glu Ile Lys Glu Asn Thr Lys Asn Asp Lys Gln Met
290                 295                 300

Val Gln Tyr Ile Tyr Lys Tyr Thr Ser Tyr Pro Asp Pro Ile Leu Leu
305                 310                 315                 320

Met Lys Ser Ala Arg Asn Ser Cys Trp Ser Lys Asp Ala Glu Tyr Gly
                325                 330                 335

Leu Tyr Ser Ile Tyr Gln Gly Gly Ile Phe Glu Leu Lys Glu Asn Asp
            340                 345                 350

Arg Ile Phe Val Ser Val Thr Asn Glu His Leu Ile Asp Met Asp His
            355                 360                 365

Glu Ala Ser Phe Phe Gly Ala Phe Leu Val Gly
            370                 375

<210> SEQ ID NO 3
<211> LENGTH: 25
<212> TYPE: DNA
<213> ORGANISM: Artificial
<220> FEATURE:
<223> OTHER INFORMATION: Primer 1

<400> SEQUENCE: 3
gggttaccag gatgtgcgtg ggggc                                          25

<210> SEQ ID NO 4
<211> LENGTH: 42
<212> TYPE: DNA
<213> ORGANISM: Artificial
<220> FEATURE:
<223> OTHER INFORMATION: Primer 2

<400> SEQUENCE: 4
gtggaggtcc ccgggggccg tgcggaaacc atttctacag tt                       42

<210> SEQ ID NO 5
<211> LENGTH: 42
<212> TYPE: DNA
<213> ORGANISM: Artificial
<220> FEATURE:
<223> OTHER INFORMATION: Primer 3

<400> SEQUENCE: 5
aactgtagaa atggtttccg cacggccccc ggggacctcc ac                       42

<210> SEQ ID NO 6
<211> LENGTH: 33
<212> TYPE: DNA
<213> ORGANISM: Artificial
<220> FEATURE:
<223> OTHER INFORMATION: Primer 4

<400> SEQUENCE: 6
atttgcggcc gcttattagc caactaaaaa ggc                                 33

<210> SEQ ID NO 7
<211> LENGTH: 44
<212> TYPE: DNA
<213> ORGANISM: Artificial
<220> FEATURE:
<223> OTHER INFORMATION: Primer 5

<400> SEQUENCE: 7
```

-continued

```
gtgagttttg tcagatttgg gctcagggcc ctcaggagtc acca                    44

<210> SEQ ID NO 8
<211> LENGTH: 44
<212> TYPE: DNA
<213> ORGANISM: Artificial
<220> FEATURE:
<223> OTHER INFORMATION: Primer 6

<400> SEQUENCE: 8
tggtgactcc tgagggccct gagcccaaat ctgacaaaac tcac                    44

<210> SEQ ID NO 9
<211> LENGTH: 39
<212> TYPE: DNA
<213> ORGANISM: Artificial
<220> FEATURE:
<223> OTHER INFORMATION: Primer 7

<400> SEQUENCE: 9
atttgcggcc gcttatcatt tacccggcag agaggagag                          39

<210> SEQ ID NO 10
<211> LENGTH: 45
<212> TYPE: DNA
<213> ORGANISM: Artificial
<220> FEATURE:
<223> OTHER INFORMATION: Primer 8

<400> SEQUENCE: 10
ataggcgcgc ccatcatcac catcatctcc actgtgtcgg ggaca                   45
```

OX40/TRAIL FUSION PROTEINS

CROSS-REFERENCE TO RELATED APPLICATIONS

This application is the U.S. national phase application filed under 35 U.S.C. §371 claiming benefit to International Patent Application No. PCT/US2010/27000, filed on Mar. 11, 2010, which is entitled to priority under 35 U.S.C. §119(e) to U.S. Provisional Patent Application No. 61/159,941 filed on Mar. 13, 2009, each of which application is hereby incorporated herein by reference in its entirety.

STATEMENT REGARDING FEDERALLY SPONSORED RESEARCH OR DEVELOPMENT

This invention was made with government support under RO1 AI 031044 and RO1 CA 074958 awarded by the National Institutes of Health. The government has certain rights in the invention.

BACKGROUND INFORMATION

A complex interplay of positive and negative signals regulates T cell activation and maintenance of T cell effector function. Members of the TNF ligand/TNF receptor superfamily figure prominently in this matrix of signals, bridging cells of the immune system, as well as with cells of other organ systems. In so doing, TNF superfamily members contribute to both tissue homeostasis and pathogenesis, via effects on cell survival and death, cellular differentiation, and inflammation. From the standpoint of autoimmune pathogenesis, interesting members of the TNF ligand superfamily are TNF-related apoptosis-inducing ligand (TRAIL) and OX40 ligand.

TRAIL binds to a number of different cognate receptors of the TNF receptor superfamily, some leading to triggering of intracellular signaling pathways and others simply acting as decoy receptors. The triggering receptors in humans are TRAIL-R1, TRAIL-R2, and osteoprotegrin, and in mice the sole triggering receptor is DR5. Virtually all cells of the immune system (T lymphocytes, B lymphocytes, natural killer cells, dendritic cells, monocytes, granulocytes) upregulate surface TRAIL and/or release soluble TRAIL stored in secretory vesicles in response to interferon and other activation signals. TRAIL inhibits autoimmunity in several animal models. Evidence for TRAIL's capacity to inhibit experimental autoimmune encephalitis (EAE), a murine model for multiple sclerosis (MS), has come from experiments invoking TRAIL−/− knockout mice, soluble TRAIL receptor (sDR5) or neutralizing anti-TRAIL mAb capable of blocking TRAIL function, and embryonic stem cell-derived dendritic cells co-expressing TRAIL and pathogenic MOG (myelin oligodendrocyte glycoprotein peptide). Interestingly, in MS patients, soluble TRAIL has emerged as a response marker for IFN-β therapy, with those most likely to respond to treatment showing early and sustained soluble TRAIL induction after therapy. Yet, TRAIL's impact on MS/EAE may be more complex, for example, the suggestion that TRAIL may promote brain cell apoptosis. Both TRAIL and FasL have been implicated in inhibition of T cells and the induction of apoptosis in T cells.

CD134, also known as the OX40 receptor, is a member of the TNF receptor superfamily, and is found predominantly on activated T-cells (Lamb et al., 1999 *Cytometry* 38: 238-243), while its ligand, OX40L (also a member of the TNF superfamily), is expressed on activated B-cells, dendritic cells and endothelial cells. OX40L:OX40 signaling is also associated with effector memory cell survival and function (Gramaglia et al., 2000 *J Immunol* 165: 3043-3050); (Soroosh et al., 2006 *J Immunol* 176: 5975-5987); (Soroosh et al., 2007 *J Immunol* 179: 5014-5023).

Multiple sclerosis is a debilitating neurological disease, and despite an expanding set of treatment options, there remains a pressing need for more effective therapeutic agents. While the precise etiology of MS is unknown, key features of its pathogenesis and clinical evolution are emerging. Pathogenic effector T cells are thought to be pivotal in driving the disease, and thus many therapeutic paths are converging on these cells, with goals such as blocking their activation and re-activation, eliminating them from the larger T cell reservoir, and interfering with their transit to sites of pathogenesis within the CNS.

Localized gene therapy in autoimmune demyelinating disease of the central nervous system (CNS) has evolved greatly over the years. Local immunogen therapy in MS and EAE has become a viable option since the lesions in these diseases are spread all over the CNS. Compared to the systemic delivery route, administering immunogens locally into the CNS has been more efficacious. Injecting naked DNA after incorporation into cationic lipid leads to transient expression. Use of replication deficient viral vectors such as adeno viral or HSV vectors has led to reliable expression of the protein and successful treatment of EAE. Gene transfer has thus become a viable option, particularly when localized expression of immunogens is desirable, such as in joints, the CNS, and other body spaces/compartments.

What is needed are fusion proteins that provide the constellation of activities associated with each of these important signaling axes, for use in the treatment of autoimmune diseases, including multiple sclerosis, for both systemic and localized administration.

SUMMARY OF THE INVENTION

Accordingly, in one aspect the present invention provides a fusion protein comprising a first domain and a second domain, wherein the first domain is a polypeptide that binds to an OX40 ligand and the second domain is a polypeptide that binds to a TRAIL receptor.

In additional aspects, the present invention is directed to pharmaceutical compositions comprising the above fusion protein, as well as methods of treating or ameliorating an autoimmune disease, alloimmune disease or cancer in a patient in need of such treatment, by administering the fusion proteins of the invention.

In a further aspect, the present invention is directed to a method of inhibiting proliferation and differentiation of T cells in a patient, the method comprising the step of administering an OX40/TRAIL fusion protein to a patient in need of such treatment.

In another aspect, the invention provides a fusion protein comprising a first domain and a second domain, wherein the first domain is a polypeptide that binds to an OX40 ligand and the second domain is a polypeptide having an inhibitory function.

The invention also provides a method of treating or ameliorating autoimmune disease, alloimmune disease or cancer in a patient by administering to the patient an effective amount of a genetic sequence encoding the fusion proteins of the present invention.

These and other aspects of the invention will become more readily apparent from the following drawings, detailed description and appended claims.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2, comprising

FIG. 2A is a schematic representation of the coding sequences for human OX40·TRAIL and human OX40·Fγ1. P1-P4 designate the locations of primers used for OX40·TRAIL assembly, while P1 and P5-P7 designate the primers used for OX40 Fcγ1 assembly. These respective chimeric coding sequences were subcloned into the pND expression vector, and both incorporate the OX40 leader sequence for in vivo expression. The P8 primer replaced P1 for the assembly in the LGFP vector used for in vitro expression of OX40·TRAIL and OX40·Fcγ1.

FIG. 2B is an image depicting Western blot analysis of OX40·TRAIL protein expression in transfectants. To this end, conditioned media generated from cells stably transfected with pOX40·TRAIL/SecTag (left lanes) or pOX40·Fcγ1/SecTag (right lanes) were run on 12% acrylamide gels and transferred to nitrocellulose membranes. These membranes were directly probed with anti-human IgG Ab (upper panel). Subsequently, membranes were stripped and re-probed with anti-human OX40 Ab (lower panel).

FIG. 3, comprising

FIG. 3A is a chart summarizing the results from experiments where mice were sensitized subcutaneously with NP-O-Su and treated after 5 days with intradermal injections into right feet of either vehicle only (2×PBS), pND vector only, pOX40·Fcγ1/ND, or pOX40·TRAIL/ND, 24 h later all mice were challenged with NP-O-Su in their right feet and vehicle (DMSO) only in their left feet. Footpads were measured after an additional 24 h. The y-axis shows the average difference in foot pad thickness between right and left feet, with N≥5 for each group. *significant ($P \leq 0.05$) difference from the empty vector group; **significant difference from both empty vector and vehicle-treated groups, both determined using one way ANOVA test.

FIG. 3B is a series of images depicting histopathological analysis was on foot pads of treated animals. There was significant edema (arrows) in right foot pads injected with the pND vector only (top right panel) or not injected with plasmid (bottom left), whereas right foot pads injected with pOX40·TRAIL/ND exhibited no significant edema (bottom right). The observed inflammation is antigen-specific since no inflammatory infiltrates or edema were observed in the unchallenged left feet (top left). The bar shown delineates 50 µm.

FIG. 3C is a chart summarizing the local immunomodulatory effect of cutaneously-expressed OX40·TRAIL. Sensitization and challenge were performed as set forth in 3A above. Only right feet of mice received pOX40·TRAIL/ND or pND, as shown, whereas both right and left feet were challenged with NP-O-Su. Footpad thickness was measured 24 h after the challenge with sensitizing agent. The y-axis shows the average difference in foot pad thickness (the thickness of the feet of naïve mice was used as the baseline), with N≥5 for each group. *significant ($P \leq 0.05$) difference between right and left feet of pND (empty) and pOX40·TRAIL/ND-treated animals, with 5 animals per group and using a one-way ANOVA test.

FIG. 4, comprising

FIG. 4A is a graph depicting results from $MOG_{38-50}$-challenged mice treated with a single intrathecal injection of plasmid lipid-DNA complexes on day 8 post-challenge. Animals were assigned clinical scores daily. The y-axis shows the mean clinical scores in pND vector only (n=9) and pOX40·TRAIL/ND (n 8) treated groups.

FIG. 4B is a chart depicting daily clinical scores added for each individual mouse in the experiment described in 4A and then averaged to yield mean cumulative clinical scores. *significant difference between pND empty vector and pOX40·TRAIL/ND treated groups ($P \leq 0.05$).

FIG. 4C is a chart depicting results from animals challenged and treated as in 4A above, except for the use of pSBC21 vector only (n=21; 3 experiments pooled) and pOX40·TRAIL/SBC21 (n=25; 3 experiments pooled). Mean clinical scores are shown. Inset: Western blot analysis of membranes probed with anti-human OX40 Ab, as described in Materials and Methods, showing expression of OX40-containing fusion proteins in conditioned media from pOX40·TRAIL/LGFP-transfected CHO-S cells (lane 1) and cerebrospinal fluid from animals injected intrathecally with pOX40·TRAIL/SBC21 (lane 2).

FIG. 4D is a chart depicting mean cumulative clinical scores calculated for the experiment in described 4C above. *significant difference (p<0.05) between the two groups was determined using a one-way ANOVA test.

FIG. 5, comprising

FIG. 5A is a chart depicting results from $MOG_{38-50}$-challenged mice treated with a single intrathecal injection on day 8 post-challenge of either pSBC21 vector only (n=10), pOX40/SBC21 (n=9), pTRAIL/SBC21 (n=9), or pOX40·TRAIL/SBC21 (n=7). Mean cumulative clinical scores were calculated based on 17 days of observation post-treatment. *significant (p<0.05) difference between the different treatment groups and the pSBC21 vector only group. **significant (p<0.005) difference between the different treatment groups and the SBC21 vector only group determined using a one-way ANOVA test.

FIG. 5B is a chart depicting results of mice described in 5A (n=3) sacrificed on day 17, perfused transcardially with PBS followed by phosphate-buffered formalin, and their spinal cords and brains were recovered for histopathological analysis. Sections stained with H&E were examined blindly and assigned scores for demyelination, monocyte/lymphocyte infiltration, and suppuration, as well as a lesion score, as described in Materials and Methods.

FIG. 5C is an image of luxol fast blue-stained sections demonstrated reduced inflammatory infiltrates (arrow) in pOX40·TRAIL/SBC21-treated mice (right panel), as compared to pSBC21 vector only-treated mice (left panel). Extensive demyelination (asterisks) was evident in both panels. The bar shown delineates 50 µm.

DETAILED DESCRIPTION

Figure 1:
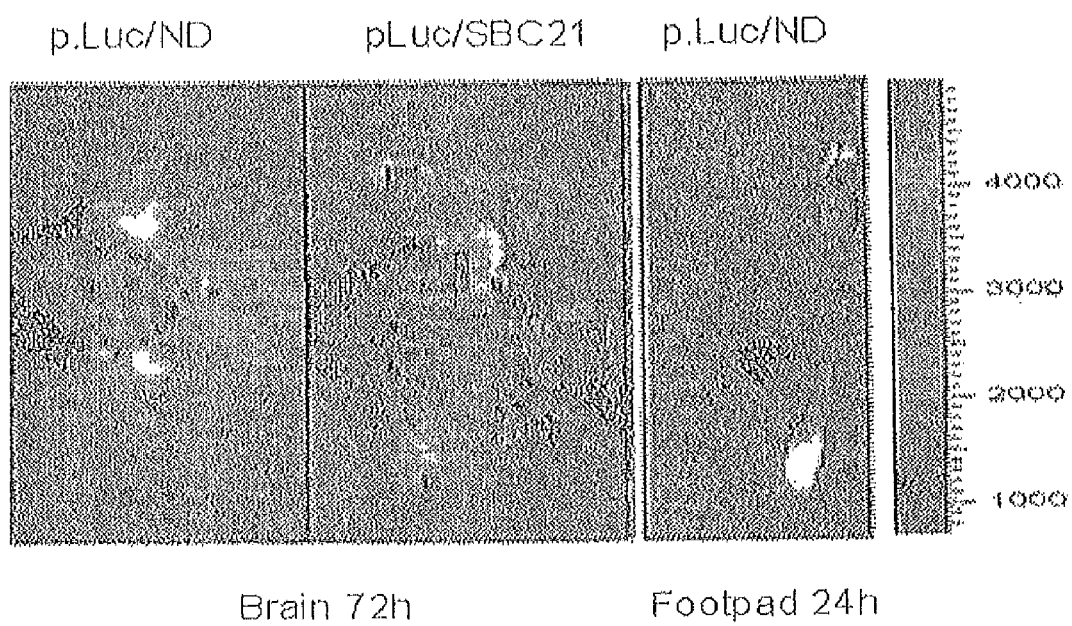
FIG. 1 is an image demonstrating that validation of intrathecal and cutaneous gene transfer Luciferase expression within the CNS was detected after intrathecal delivery of pLuc/ND (left panel) and transposon-based pLuc/SBC21 (middle panel) 72 h post-injection of the respective expression plasmids. Luciferase expression in the footpad was detected 24 h after intradermal injection of pLuc/ND (right panel).

This invention relates to OX40/TRAIL and related fusion proteins, and methods of treating autoimmune diseases and cancer with these proteins.

In one aspect the present invention provides a fusion protein comprising a first domain and a second domain, wherein the first domain is a polypeptide that binds to an OX40 ligand and the second domain is a polypeptide that binds to a TRAIL receptor.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "fusion proteins" refers to chimeric proteins comprising amino acid sequences of two or more different proteins. Typically, fusion proteins result from in vitro recombinatory techniques well known in the art.

As used herein, "biologically active or immunologically active" refers to fusion proteins according to the present invention having a similar structural function (but not necessarily to the same degree), and/or similar regulatory function (but not necessarily to the same degree), and/or similar biochemical function (but not necessarily to the same degree) and/or immunological activity (but not necessarily to the same degree) as the individual wild type proteins which are the building blocks of the fusion proteins of the present invention.

As used herein, a "deletion" is defined as a change in amino acid sequence in which one or more amino acid residues are absent as compared to the wild-type protein.

As used herein an "insertion" or "addition" is a change in an amino acid sequence that has resulted in the addition of one or more amino acid residues as compared to the wild-type protein.

As used herein "substitution" results from the replacement of one or more amino acids by different amino acids, respectively, as compared to the wild-type protein.

As used herein, the term "variant" means any polypeptide having a substitution of, deletion or addition of one (or more) amino acid from or to the sequence, including allelic variations, as compared with the wild-type protein, so long as the resultant variant fusion protein retains at least 75%, 80%, 85%, 90%, 95%, 99% or more of the biological or immunologic activity as compared to the wild-type proteins as used in the present invention. Additionally, while in general it is desirable for variants to show enhanced ability for binding to a given molecule, in some embodiments variants may be designed with slightly reduced activity as compared to other fusion proteins of the invention, for example, in instances in which one would purposefully want to attenuate activity, for example, to diminish neurotoxicity. Moreover, variants or derivatives can be generated that would bind more selectively to one of the TRAIL receptor variants (there are three TRAIL receptors in humans). Furthermore, variants or derivatives can be generated that would have altered multimerization properties. When engineering variants, this could be done for either the entire TRAIL extracellular domain, or for that component of the extracellular domain that is incorporated within the fusion protein itself.

Preferably, variants or derivatives of the fusion proteins of the present invention maintain the hydrophobicity/hydrophilicity of the amino acid sequence. Conservative amino acid substitutions may be made, for example from 1, 2 or 3 to 10, or 30 substitutions provided that the modified sequence retains the ability to act as a fusion protein in accordance with present invention. Amino acid substitutions may include the use of non-naturally occurring analogues, for example to increase blood plasma half-life.

Conservative substitutions are known in the art, for example according to the table below. Amino acids in the same block in the second column and preferably in the same line in the third column may be substituted for each other:

| ALIPHATIC | Non-polar | GAP ILV |
|---|---|---|
|  | Polar - uncharged | CSTM NQ |
|  | Polar - charged | DE KR |
| AROMATIC |  | HFWY |

The term "derivative" as used herein in relation to the amino acid sequence means chemical modification of a fusion protein of the invention.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used, "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "polypeptide" as used herein is defined as a chain of amino acid residues, usually having a defined sequence. As used herein the term polypeptide is mutually inclusive of the terms "peptide" and "protein".

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

As used herein, a "therapeutically effective amount" is the amount of a therapeutic composition sufficient to provide a beneficial effect to a mammal to which the composition is administered.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

The term "vaccine" as used herein is defined as a material used to provoke an immune response after administration of the material to a mammal.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The term "virus" as used herein is defined as a particle consisting of nucleic acid (RNA or DNA) enclosed in a protein coat, with or without an outer lipid envelope, which is capable of replicating within a whole cell.

As used herein in the specification and claims, including as used in the examples and unless otherwise expressly specified, all numbers may be read as if prefaced by the word "about", even if the term does not expressly appear. Also, any numerical range recited herein is intended to include all subranges subsumed therein. Where any amino acid sequence is specifically referred to by a Swiss Prot. or NCBI Accession number, the sequence is incorporated herein by reference.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides, in one aspect, a fusion protein that acts on the OX40L and TRAIL signaling axis, for example a fusion protein having a first domain that comprises a polypeptide that binds to an OX40 ligand; and a second domain that comprises a polypeptide that binds to a TRAIL receptor. In particular, the first domain is a polypeptide that has the capacity to interfere with OX40 ligand's ability to trigger through its OX40 receptor, and the second domain is a polypeptide that can direct inhibitory signals through cognate receptors on T cells or other cells bearing a TRAIL receptor.

Suitable first domains in the context of the OX40L/TRAIL signaling axis include, for example, the OX40 protein itself, variants or derivatives of the wild-type OX40 protein, or other polypeptides or proteins specifically tailored to bind OX40 ligand and prevent this ligand from signaling through its OX40 receptor, such as antibodies that bind to OX40 ligand, parts of antibodies that bind to OX40 ligand, and lipocalin derivatives engineered to bind to OX40 ligand. Preferably, the first domain of the fusion protein of this embodiment is at least a portion of the extracellular domain of the OX40 protein, specifically that portion of the extracellular domain which is necessary for binding to the OX40 ligand and interfering with its ability to bind and trigger a membrane-bound OX40 receptor. Variants of the wild-type form of the extracellular domain are also included in the present invention, or the portion of the extracellular domain responsible for OX40L binding, so long as the variant provides a similar level of biological activity as the wild-type protein.

Accordingly, the term "polypeptide that binds to an OX40 ligand" as used herein includes the OX40 protein; the extracellular domain of the OX40 protein; a polypeptide which is at least a portion of the extracellular domain of the OX40 protein, the portion responsible for binding to an OX40 ligand; antibodies to OX40 ligand; lipocalins engineered to bind to OX40 ligand; and variants and/or derivatives of any of these. The term "OX40" is understood to embrace a polypeptide which is the complete amino acid sequence of the OX40 protein, including the cytoplasmic, transmembrane and extracellular domains, as well as polypeptides which are smaller portions of the protein, such as the extracellular domain, or a portion of the extracellular domain. In one embodiment the first domain in the OX40/TRAIL signaling pair is at least a portion of the extracellular domain of a human OX40 receptor.

Suitable second domains in the context of the OX40/TRAIL signaling axis include, for example, the TRAIL protein itself, variants or derivatives of the TRAIL protein, or other polypeptides or proteins that are specifically designed to inhibit activation of T cells or other cells and/or induce apoptosis through the TRAIL receptor, such as agonistic anti-TRAIL Ab, and variants and/or derivatives of these. Preferably, the second domain of the fusion protein in this embodiment is at least a portion of the extracellular domain of the TRAIL protein, specifically that portion which is necessary for binding to a TRAIL receptor. Variants of the wild-type form of the extracellular domain of the TRAIL protein, or the portion of the extracellular domain responsible for TRAIL receptor binding, are also included in the present invention, so long as the variant provides a similar level of biological activity as the wild-type protein.

Accordingly, the term "polypeptide that binds to a TRAIL receptor" as used herein includes the TRAIL protein; the extracellular domain of the TRAIL protein; a polypeptide which is at least a portion of the extracellular domain of the TRAIL protein, the portion responsible for binding to a TRAIL receptor; antibodies to a TRAIL receptor; lipocalins engineered to bind to a TRAIL receptor; and variants and/or derivatives of any of these. The term "TRAIL" is understood to embrace polypeptides corresponding to the complete amino acid sequence of the TRAIL protein, including the cytoplasmic, transmembrane and extracellular domains, as well as polypeptides corresponding to smaller portions of the protein, such as the extracellular domain, or a portion of the extracellular domain. In one embodiment the second domain of the OX40/TRAIL signaling pair is at least a portion of the extracellular domain of the human TRAIL protein.

In one embodiment, the present invention comprises an OX40/TRAIL fusion protein. In another embodiment, the term "OX40/TRAIL fusion protein" refers to the specific fusion protein identified by SEQ. ID. NO. 1

HUMAN OX40-TRAIL

SEQ. ID. NO. 1

MCVGARRLGRGPCAALLLLGLGLSTVTGLHCVGDTYPSNDRCCHECRPG

NGMVSRCSRSQNTVCRPCGPGFYNDVVSSKPCKPCTWCNLRSGSERKQL

CTATQDTVCRCRAGTQPLDSYKPGVDCAPCPPGHFSPGDNQACKPWTNC

TLAGKHTLQPASNSSDAICEDRDPPATQPQETQGPPARPITVQPTEAWP

RTSQGPSTRPVEVPGGRAETISTVQEKQQNISPLVRERGPQRVAAHITG

TRGRSNTLSSPNSKNEKALGRKINSWESSRSGHSFLSNLHLRNGELVIH

EKGFYYIYSQTYFRFQEEIKENTKNDKQMVQYIYKYTSYPDPILLMKSA

RNSCWSKDAEYGLYSIYQGGIFELKENDRIFVSVTNEHLIDMDHEASFF

GAFLVG

In another embodiment, the term "OX40/TRAIL fusion protein" refers to the specific fusion protein identified by SEQ. ID. NO. 2

HUMAN OX40-TRAIL

SEQ. ID. NO. 2

MCVGARRLGRGPCAALLLLGLGLSTVTGLHCVGDTYPSNDRCCHECRPG

NGMVSRCSRSQNTVCRPCGPGFYNDVVSSKPCKPCTWCNLRSGSERKQL

CTATQDTVCRCRAGTQPLDSYKPGVDCAPCPPGHFSPGDNQACKPWTNC

TLAGKHTLQPASNSSDAICEDRDPPATQPQETQGPPARPITVQPTEAWP

-continued

RTSQGPSTRPVEVPGGRARGPQRVAAHITGTRGRSNTLSSPNSKNEKAL

GRKINSWESSRSGHSFLSNLHLRNGELVIHEKGFYYIYSQTYFRFQEEI

KENTKNDKQMVQYIYKYTSYPDPILLMKSARNSCWSKDAEYGLYSIYQG

GIFELKENDRIFVSVTNEHLIDMDHEASFFGAFLVG

Both SEQ. ID. NO. 1 and SEQ. ID. NO. 2 include original signal peptides; these signal peptides can be varied according to the needs of the user, the expression system, and other factors, as would be understood by one skilled in the art. Signal peptides are well known in the art, and any desired signal peptide can be used, including those recognized/predicted by publicly available signal peptide recognition software known to those skilled in the art.

In additional embodiments, the OX40/TRAOL fusion protein is a variant and/or derivative of the amino acid sequence shown in SEQ. ID. NO. 1. In yet an additional aspect of the present invention, the TRAIL component of any of the fusion proteins described herein can be substituted with another inhibitory protein, i.e. a protein which prevents activation of an immune response and/or induces apoptosis, anergy, and/or any other form of non-responsiveness in T cells or other cell types, such as B cells, natural killer (NK) cells, NKT cells, lymphoid progenitor cells, dendritic cells, monocytes/macrophages, tissue-based macrophage lineage cells with antigen-presenting capacity, and any one of a number of non-professional antigen-presenting cells, for example, endothelial cells. Examples of inhibitory proteins include, but are not limited to, FasL, TNF, PDL-1, PDL-2, B7x, B7-H3 and CD31.

For example, BTLA is an important inhibitory receptor, and B7x may be the ligand, in addition to other ligands as yet to be discovered. Similarly, CTLA-4 is another important inhibitory receptor, and ligands that drive this inhibitory CTLA-4 receptor include some of the B7 molecules, as well as agonist Ab. In this case the fusion proteins would by OX40/B7x and OX40/B7 agonist fusion proteins, respectively.

There is growing appreciation that B cells may also be key for driving autoimmunity. Additional inhibitory ligands (fused to Fn14) that drive B cell inhibitory receptors, such as CD100 (binds to CD72), CD5 (also binds to CD72), CD72 (binds to CD5), Ep-CAM (binds to LAIR-1), agonists for Fc-gamma-RII, CD22, PDL-1, PDL-2, CD66a, and PIR-B are also included within the scope of the present invention.

The literature is replete with additional examples, such as those listed in Sinclair, N. "*Why so Many Coinhibitory Receptors*?, Scand. J. Immunol, 50, 10-13 (1999); Melero, I. et al. "*Immunostimulatory monoclonal antibodies for cancer therapy*", Nature Rev. Cancer 7:95-106 (2007); and Zang, X. et al., "*The B7 Family and Cancer Therapy: Costimulation and Coinhibition*", Clin. Cancer Res. 13: 5271-5279 (2007), all incorporated herein by reference. Any of the above mentioned inhibitory proteins are embraced by the fusion proteins and methods of the present invention, and are referred to herein collectively as "polypeptides having an inhibitory function".

Accordingly, in additional embodiments the present invention provides OX40/inhibitory protein fusion pairs, such as OX40/FasL, OX40/PDL-1, OX40/PDL-2, OX40/TNF, OX40/CD100, OX40/CD5, OX40/CD72, OX40/Ep-CAM, OX40/Fc-gamma-RII, OX40/CD22, OX40/CD66a, OX40/PIR-B, OX40/B7x, OX40/B7-H3 and OX40/CD31. Any of the first domains described above in the context of the OX40/TRAIL signaling axes, e.g. polypeptides that bind to a OX40 ligand, would be suitable first domains in these embodiments.

In one embodiment, the fusion proteins of the present invention inhibit activation of the immune system by preventing or reducing proliferation and differentiation of myelin-specific T cells. In some embodiments the fusion proteins of the present invention inhibit production of pro-inflammatory cytokines and chemokines, such as IL-6, IL-8, RANTES, IP-10, and MCP-1, or inhibit potentiation of other cytokines/chemokines, such as TNF-α, and IL-1β; or inhibit induction of matrix metalloproteinases such as MMP-1 and MMP-9; or inhibit prostaglandin E2 secretion from fibroblasts and synoviocytes. The present invention embraces inhibition/down-regulation of any and all cytokines that are either promoted by OX40 ligand or down-modulated by the TRAIL ligand.

In other embodiments the fusion proteins of the present invention inhibit autoreactive T cell proliferation, autoreactive antibody production, and inflammatory reactions.

Most (although not all) of the TNF receptor (TNFR) superfamily members are type II transmembrane proteins. These proteins contain an extracellular domain that is structurally characterized by the presence of one to six cysteine-rich domains (CRDs). The typical CRD is approximately 40 amino acids in length and contains six conserved cysteine residues that form three intrachain disulphide bridges. The CRD itself is typically composed of two distinct structural modules.

TRAIL

TRAIL is a Type II membrane protein having 291 amino acids and has been sequenced in a number of species, including, but not limited to, mouse: Swiss Prot. Accession No. P50592: human: Swiss Prot. Accession No. P50591; *Rattus norvegicus*: NCBI Accession NP_663714; *Siniperca Chuatsi* (Chinese Perch): NCBI Accession AAX77404; *Gallus Gallus* (Chicken): NCBI Accession BAC79267; Sus Scrofa (Pig): NCBI Accession NP_001019867; *Ctenopharyngodon Idella* (Grass Carp): NCBI Accession AAW22593; and *Bos Taurus* (Cattle): NCBI Accession XP_001250249.

The extracellular domain of TRAIL comprises amino acids 39-281, and the TNF domain responsible for receptor binding is amino acid 121-280, based on TNF homology models. The portion of the protein that is particularly important for conferring activity has been identified. See, e.g., "*Triggering cell death: The crystal structure of Apo2L/TRAIL in a complex with death receptor*", Hymowitz S G, et al., Am. Mol. Cell. 1999 October; 4(4):563-71), incorporated herein by reference, which reports the most important amino acids for TRAIL binding to its receptor and activity are amino acids around the zinc area such as aa (191-201-205-207-236-237) and amino acids (150-216), incorporated herein by reference. See also 1) Krieg A et al 2003 Br. J of Cancer 88: 918-927, which describes two human TRAIL variants without apoptotic activity, TRAIL-γ and TRAIL β; 2) "*Enforced covalent trimerization increases the activity of the TNF ligand family members TRAIL and CD95L*", D Berg et al., *Cell death and differentiation* (2007)14, 2021-2034; and 3) "*Crystal Structure of TRAIL-DR5 complex identifies a critical role of the unique frame insertion in conferring recognition specificity*", S. Cha et al., J. Biol. Chem. 275: 31171-31177 (2000), all incorporated herein by reference.

OX40

OX40, a member of the TNFR superfamily, is a polypeptide of 277 amino acids in length. The extracellular region is amino acids 29-214, with amino acids 31-166 of this being the TNFR homology region, with three CRDs. The structure and some critical binding sites of OX40 and OX40 ligand have been determined. Compaan, D. et al., "*The crystal structure of the Costimulatory OX40-OX40L complex*", Structure 14: 1321-1330 (2006), incorporated herein by reference. The CRDs of OX40 appear to be important for receptor binding of the OX40 ligand, including CRD1, aa 30-65; CRD2, aa 67-81 and CRD3, aa 109-125. OX40 has been sequenced in a number of different species, including, but not limited to, mouse: Swiss Prot. Accession No. P47741: human: Swiss Prot. Accession No. P43489; and rat: Swiss Prot. Accession No. 15725.

Modification

This invention relates to OX40/TRAIL and related fusion proteins. The invention also encompasses variants of the fusion proteins. While in general it is desirable for variants to show enhanced ability for binding to a given molecule, in some embodiments variants may be designed with slightly reduced activity as compared to other fusion proteins of the invention, for example, in instances in which one would purposefully want to attenuate activity. Moreover, variants or derivatives can be generated that would bind more selectively to one of the TRAIL receptor variants (there are three TRAIL receptors in humans). Furthermore, variants or derivatives can be generated that would have altered multimerization properties. When engineering variants, this could be done for either the entire TRAIL extracellular domain, or for that component of the extracellular domain that is incorporated within the fusion protein itself.

Preferably, variants or derivatives of the fusion proteins of the present invention maintain the hydrophobicity/hydrophilicity of the amino acid sequence.

The invention also provides chemical modification of a fusion protein of the invention. Non-limiting examples of such modifications may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Additional modifications can include, for example, production of a fusion protein conjugated with polyethylene glycol (PEG), or addition of PEG during chemical synthesis of a polypeptide of the invention. Modifications of polypeptides or portions thereof can also include reduction/alkylation; chemical coupling to an appropriate carrier or mild formalin treatment.

Other derivatives of the fusion proteins of the present invention include incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Derivatives also include polypeptides modified by glycosylation. These can be made by modifying glycosylation patterns during synthesis and processing in various alternative eukaryotic host expression systems, or during further processing steps. Methods for producing glycosylation modifications include exposing the fusion proteins to glycosylating enzymes derived from cells that normally carry out such processing, such as mammalian glycosylation enzymes. Alternatively, deglycosylation enzymes can be used to remove carbohydrates attached during production in eukaryotic expression systems. Additionally, one can also modify the coding sequence so that glycosylation site(s) are added or glycosylation sites are deleted or disabled. Furthermore, if no glycosylation is desired, the proteins can be produced in a prokaryotic host expression system.

Variants and/or derivatives of the fusion proteins of the invention can be prepared by chemical synthesis or by using site-directed mutagenesis [Gillman et al., Gene 8:81 (1979); Roberts et al., Nature 328:731 (1987) or Innis (Ed.), 1990, PCR Protocols: A Guide to Methods and Applications, Academic Press, New York, N.Y.] or the polymerase chain reaction method [PCR; Saiki et al., Science 239:487 (1988)], as exemplified by Daugherty et al. [Nucleic Acids Res. 19:2471 (1991)] to modify nucleic acids encoding the complete receptors.

Additional modifications can be introduced such as those that further stabilize the TRAIL trimer and/or increase affinity of binding to the TRAIL receptor; and spacers/linkers can be added to alter the distance between the two structural components of the fusion protein, as well as alter the flexibility of this region. In additional embodiments, the fusion proteins of the present invention may further comprise one or more additional polypeptide domains added to facilitate protein purification, to increase expression of the recombinant protein, or to increase the solubility of the recombinant protein. Such purification/expression/solubility facilitating domains include, but are not limited to, metal chelating peptides such as histidine-tryptophan modules that allow purification on immobilized metals (Porath J (1992) Protein Expr Purif 3-0.26328 1), protein A domains that allow purification on immobilized immunoglobulin, and the domain utilized in the FLAGS extension/affinity purification system (Immunex Corp, Seattle, Wash.). The inclusion of a cleavable linker sequence such as Factor Xa or enterokinase (Invitrogen, San Diego, Calif.) between the purification domain and OX40/TRAIL is useful to facilitate purification.

Additional fusion expression vectors include pGEX (Pharmaci, a Piscataway, N.J.), pMAL (New England Biolabs, Beverly, Mass.) and pRITS (Pharmacia, Piscataway, N.J.) which fuse glutathione S transferase (GST), maltose B binding protein, or protein A, respectively, to the target recombinant protein. EBV, BKV, and other episomal expression vectors (Invitrogen) can also be used. In addition, retroviral and lentiviral expression vectors can also be used. Furthermore, any one of a number of in vivo expression systems designed for high level expression of recombinant proteins within organisms can be invoked for producing the fusion proteins specified herein.

In another embodiment a fusion protein of the present invention may contain a heterologous signal sequence at its N-terminus. In certain host cells (e.g., mammalian host cells), expression and/or secretion of the fusion protein can be increased through use of a heterologous signal sequence. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described polypeptides having a signal sequence, as well as to polypeptides from which the signal sequence has been proteolytically cleaved (i.e., the cleavage products).

In order to enhance stability and/or reactivity, the fusion proteins of the present invention can also be modified to incorporate one or more polymorphisms in the amino acid sequence resulting from natural allelic variation. Additionally, D-amino acids, non-natural amino acids or non-amino acid analogues can be substituted or added to produce a modified fusion protein within the scope of this invention.

The amino acid sequences of the present invention may be produced by expression of a nucleotide sequence coding for same in a suitable expression system.

In addition, or in the alternative, the fusion protein itself can be produced using chemical methods to synthesize the desired amino acid sequence, in whole or in part. For example, polypeptides can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic polypeptides may be confirmed by amino acid analysis or sequencing (e.g., the Edman degradation procedure). Additionally, the amino acid sequence of a fusion protein of the invention, or any part thereof, may be altered during direct synthesis and/or combined using chemical methods with a sequence from other subunits, or any part thereof, to produce a variant polypeptide.

Assays for measuring the immunologic activity of any homolog, derivative or variant of any fusion protein of the present invention are well known in the art.

For example, any one of several conventional assays for monitoring cytokine production, as a measure of immune cells activation and differentiation, can be invoked. For example, for tracking T cell activation, interleukin-2 can be employed as a marker, which can be assayed as described in Proc. Natl. Acad. Sci. USA. 86:1333 (1989) the pertinent portions of which are incorporated herein by reference. A kit for an assay for the production of interferon is also available from Genzyme Corporation (Cambridge, Mass.). One can also employ immunofluorescence and flow cytometry to monitor cytokine production on a cellular basis, and to monitor cell surface markers that reflect cellular activation and/or differentiation states. A host of such markers are known, detecting antibodies are broadly commercially available, and the markers are well known in the art.

A common assay for T cell proliferation entails measuring tritiated thymidine incorporation. The proliferation of T cells can be measured in vitro by determining the amount of $^3$H-labeled thymidine incorporated into the replicating DNA of cultured cells. Therefore, the rate of DNA synthesis and, in turn, the rate of cell division can be quantified.

Another assay for monitoring T cell proliferation is based on loading T cells with the CFSE dye, and subsequently monitoring by flow cytometry the dilution of this dye that accompanies successive cell divisions. In addition to monitoring the inhibition of T cell proliferation, the bioactivity of the fusion protein can also be monitored by evaluating its capacity to induce apoptosis in TRAIL receptor-positive tumor cell lines in which TRAIL receptor triggering leads to apoptosis. By combining these cells with other cells that have OX40L on their surfaces, one can assess whether new fusion protein derivatives both anchor to OX40L and thereby have their pro-apoptotic TRAIL-driven activity enhanced in this way.

Pharmaceutical Compositions and Dosing Regimens.

Administration of the compositions of this invention is typically parenteral, by intravenous, subcutaneous, intramuscular, or intraperitoneal injection, or by infusion or by any other acceptable systemic method. Administration by intravenous infusion, typically over a time course of about 1 to 5 hours, is preferred. In addition, there are a variety of oral delivery methods for administration of therapeutic proteins, and these can be applied to the therapeutic fusion proteins of this invention.

Often, treatment dosages are titrated upward from a low level to optimize safety and efficacy. Generally, daily dosages will fall within a range of about 0.01 to 20 mg protein per kilogram of body weight. Typically, the dosage range will be from about 0.1 to 5 mg protein per kilogram of body weight. Various modifications or derivatives of the fusion proteins, such as addition of polyethylene glycol chains (PEGylation), may be made to influence their pharmacokinetic and/or pharmacodynamic properties.

To administer the fusion protein by other than parenteral administration, it may be necessary to coat the protein with, or co-administer the protein with, a material to prevent its inactivation. For example, protein may be administered in an incomplete adjuvant, co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) J. Neuroimmunol. 7:27).

An "effective amount" of a composition of the invention is an amount that will ameliorate one or more of the well known parameters that characterize medical conditions caused by autoimmune diseases such as multiple sclerosis. Many such parameters and conditions have been described. An effective amount, in the context of multiple sclerosis, will be the amount of fusion protein that is sufficient to accomplish one or more of the following: decrease the severity of symptoms; decrease the duration of disease exacerbations; increase the frequency and duration of disease remission/symptom-free periods; prevent fixed impairment and disability; and/or prevent/attenuate chronic progression of the disease. Clinically, this would result in improvement in visual symptoms (visual loss, diplopia), gait disorders (weakness, axial instability, sensory loss, spasticity, hyperreflexia, loss of dexterity), upper extremity dysfunction (weakness, spasticity, sensory loss), bladder dysfunction (urgency, incontinence, hesitancy, incomplete emptying), depression, emotional lability, and cognitive impairment. Pathologically the treatment with fusion proteins of the present invention reduces one or more of the following, such as myelin loss, breakdown of the blood-brain barrier, perivascular infiltration of mononuclear cells, immunologic abnormalities, gliotic scar formation and astrocyte proliferation, metalloproteinase production, and impaired conduction velocity.

Although the compositions of this invention can be administered in simple solution, they are more typically used in combination with other materials such as carriers, preferably pharmaceutical carriers. Useful pharmaceutical carriers can be any compatible, non-toxic substance suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. Remington's Pharmaceutical Science, 17th Ed. (Mack Publishing Company, Easton, Pa., 1990). Alternatively, compositions of the invention may be introduced into a patient's body by implantable drug delivery systems [Urquhart et al., Ann. Rev. Pharmacol. Toxicol. 24:199 (1984)].

Therapeutic formulations may be administered in many conventional dosage formulations. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), The Pharmacological Bases of Therapeutics, 8th Ed., Pergamon Press; and Remington's Pharmaceutical Sciences, supra, Easton, Pa.; Avis et al. (eds.) (1993) Pharmaceutical Dosage Forms: Parenteral Medications Dekker, N.Y.; Lieberman et al. (eds.) (1990) Pharmaceutical Dosage Forms: Tablets Dekker, N.Y.; and Lieberman et al. (eds.) (1990), Pharmaceutical Dosage Forms: Disperse Systems Dekker, N.Y.

In additional embodiments, the present invention contemplates administration of the fusion proteins by gene therapy methods, e.g., administration of an isolated nucleic acid encoding a fusion protein of interest. The protein building blocks (e.g., first and second domains) of the fusion proteins of the present invention have been well-characterized, both as to the nucleic acid sequences encoding the proteins and the resultant amino acid sequences of the proteins. Engineering of such isolated nucleic acids by recombinant DNA methods is well within the ability of one skilled in the art. Codon optimization, for purposes of maximizing recombinant protein yields in particular cell backgrounds, is also well within the ability of one skilled in the art. Administration of an isolated nucleic acid encoding the fusion protein is encompassed by the expression "administering a therapeutically effective amount of a fusion protein of the invention". Gene therapy methods are well known in the art. See, e.g., WO96/07321 which discloses the use of gene therapy methods to generate intracellular antibodies. Gene therapy methods have also been successfully demonstrated in human patients. See, e.g., Baumgartner et al., Circulation 97: 12, 1114-1123 (1998), and more recently, Fatham, C. G. 'A gene therapy approach to treatment of autoimmune diseases', Immun. Res. 18:15-26 (2007); and U.S. Pat. No. 7,378,089, both incorporated herein by reference. See also Bainbridge J W B et al. "*Effect of gene therapy on visual function in Leber's congenital Amaurosis*". N Engl Med 358:2231-2239, 2008; and Maguire A M et al. "*Safety and efficacy of gene transfer for Leber's. Congenital Amaurosis*". *N Engl J Med* 358:2240-8, 2008. There are two major approaches for introducing a nucleic acid encoding the fusion protein (optionally contained in a vector) into a patients cells; in vivo and ex vivo. For in vivo delivery the nucleic acid is injected directly into the patient, usually at the site where the fusion protein is required. For ex vivo treatment, the patient's cells are removed, the nucleic acid is introduced into these isolated cells and the modified cells are administered to the patient either directly or, for example, encapsulated within porous membranes which are implanted into the patient (see, e.g., U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. Commonly used vectors for ex vivo delivery of the gene are retroviral and lentiviral vectors.

Preferred in vivo nucleic acid transfer techniques include transfection with viral vectors such as adenovirus, Herpes simplex I virus, adeno-associated virus), lipid-based systems (useful lipids for lipid-mediated transfer of the gene are DOTMA, DOPE and DC-Chol, for example), naked DNA, and transposon-based expression systems. For review of the currently known gene marking and gene therapy protocols see Anderson et al., Science 256:808-813 (1992). See also WO 93/25673 and the references cited therein.

"Gene therapy" includes both conventional gene therapy where a lasting effect is achieved by a single treatment, and the administration of gene therapeutic agents, which involves the one time or repeated administration of a therapeutically effective DNA or mRNA. Oligonucleotides can be modified to enhance their uptake, e.g. by substituting their negatively charged phosphodiester groups by uncharged groups. OX40/TRAIL fusion proteins of the present invention can be delivered using gene therapy methods, for example locally in tumor beds, intrathecally, or systemically (e.g., via vectors that selectively target specific tissue types, for example, tissue-specific adeno-associated viral vectors). In some embodiments, primary cells (such as lymphocytes or stem cells) from the individual can be transfected ex vivo with a gene encoding any of the fusion proteins of the present invention, and then returning the transfected cells to the individual's body.

In some embodiments, the fusion proteins of the present invention are suitable for treatment of immune system diseases or disorders, including, but not limited to, autoimmune hemolytic anemia, autoimmune neonatal thrombocytopenia, idiopathic thrombocytopenia purpura, autoimmune neutropenia, autoimmunocytopenia, hemolytic anemia, antiphospholipid syndrome, dermatitis, gluten-sensitive enteropathy, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendo-crinopathies, Purpura (e.g., Henloch-Scoenlein purpura), Reiter's Disease, Stiff-Man Syndrome, Autoimmune Pulmonary Inflammation, myocarditis, IgA glomerulonephritis, dense deposit disease, rheumatic heart disease, Guillain-Barre Syndrome, insulin dependent diabetes mellitus, and autoimmune inflammatory eye, autoimmune thyroiditis, hypothyroidism (i.e., Hashimoto's thyroiditis), systemic lupus erythematosus, discoid lupus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes mellitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulomatous, degenerative, and atrophic disorders).

In one embodiment, the fusion proteins of the present invention are used to treat multiple sclerosis.

In additional embodiments, the fusion proteins of the present invention can be used to treat various types of cancer. Soluble TRAIL has been associated with the induction of apoptosis in certain kinds of tumor cells. Moreover, for certain tumor types, inflammation may actually be pro-tumorigenic. Hence, a TRAIL fusion protein can be used to kill tumor cells directly, block pro-tumorigenic inflammation, and furthermore, can be used to block angiogenesis. The OX40 component (the first domain) in this case would localize the TRAIL to OX40 ligand-positive cells (for example, on tumor endothelium and/or on tumor cells themselves).

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. More particular examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

"Treating" or "treatment" or "alleviation" refers to both therapeutic treatment and prophylactic or preventative measures, wherein the object is to prevent or slow down (lessen) the targeted pathologic condition or disorder. A subject is successfully "treated" if, after receiving a therapeutic amount of a fusion protein of the invention according to the methods of the present invention, the subject shows observable and/or measurable reduction in or absence of one or more signs and symptoms of the particular disease. For example, for cancer, reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues. Reduction of the signs or symptoms of a disease may also be felt by the patient. Treatment can achieve a complete response, defined as disappearance of all signs of cancer, or a partial response, wherein the size of the tumor is decreased, preferably by more than 50%, more preferably by 75%. A patient is also considered treated if the patient experiences stable disease. In a preferred embodiment, the cancer patients are still progression-free in the cancer after one year, preferably after 15 months. These parameters for assessing successful treatment and improvement in the disease are readily measurable by routine procedures familiar to a physician of appropriate skill in the art.

In further embodiments, the fusion proteins of the present invention can be used to treat alloimmune diseases, for example graft rejection, or graft-versus-host or host-versus-graft disease.

EXAMPLES

The invention is now described with reference to the following Examples. These Examples are provided for the purpose of illustration only, and the invention is not limited to these Examples, but rather encompasses all variations which are evident as a result of the teachings provided herein.

The materials and methods employed in the experiments disclosed herein are now described.

Plasmid Constructs:

Coding sequence for the extracellular domain of human OX40 (29-214) was linked in-frame to that for the extracellular domain of human TRAIL (98-281) This chimerization was achieved via PCR assembly, using EST clones from ATCC as templates (Huang et al. 2001 *Int Immunol* 13: 529-539). The primers used for this assembly were as follows:

```
P1:
                                          (SEQ ID NO: 3)
GGGTTACCAGGATGTGCGTGGGGGC

P2:
                                          (SEQ ID NO: 4)
GTGGAGGTCCCCGGGGGCCGTGCGGAAACCATTTCTACAGTT

P3:
                                          (SEQ ID NO: 5)
AACTGTAGAAATGGTTTCCGCACGGCCCCCGGGGACCTCCAC

P4:
                                          (SEQ ID NO: 6)
ATTTGCGGCCGCTTATTAGCCAACTAAAAAGGC

P5:
                                          (SEQ ID NO: 7)
GTGAGTTTTGTCAGATTTGGGCTCAGGGCCCTCAGGAGTCACCA

P6:
                                          (SEQ ID NO: 8)
TGGTGACTCCTGAGGGCCCTGAGCCCAAATCTGACAAAACTCAC

P7:
                                          (SEQ ID NO: 9)
ATTTGCGGCCGCTTATCATTTACCCGGCAGAGAGGAGAG

P8:
                                          (SEQ ID NO: 10)
ATAGGCGCGCCCATCATCACCATCATCTCCACTGTGTCGGGGACA
```

For in vivo expression, both the pND plasmid and the transposon-based 'sleeping beauty' SBC21 plasmid system were employed (Ivies et al., 1997 *Cell* 91: 501-510). As is evident from the primer sequences above, a KpnI restriction enzyme site was incorporated into the P1 primer, and a NoI site was incorporated into the P4 and P7 primers, for pND subcloning. For pSBC21 subcloning, a HindIII site was substituted for the NotI site in the P4 and P7 primers. PCR products were ligated into the pCR2.1 plasmid by TA cloning (Invitrogen, Carlsbad, Calif.). Constructs were digested with KpnI and NotI, and the moblilized cassettes were ligated into the corresponding sites of pND. The pND vector, originally a kind gift from Gary Rhodes (UC-Davis), has a pUC19 backbone, a CMV promoter including intron A (Chapman et al., 1991 *Nucleic Acids Res* 19: 3979-3986), and subcloned BGH introns. For purposes of pSBC21 subcloning, OX40-TRAIL coding sequence, mobilized by KpnI/HindIII digestion, was ligated into the corresponding sites of the pMF vector, which contains the EF1α promoter. Subsequently the EF1α-OX40-TRAIL cassette was subcloned into pSBC21, after digestion with NotI.

For verifying intrathecal activity of the pND and pSBC21 expression plasmids, luciferase reporter constructs pLuc/ND and pLuc/SBC21 were produced using similar subcloning strategies. Specifically, for the pND expression vector, coding sequence for firefly (*Photinus pyralis*) luciferase was subcloned from pGL2 (Promega, Madison, Wis.) and ligated into pND using the SalI and NotI sites. For the pSBC2'-based luciferase expression construct, the luciferase coding sequence from pTAL-Luc (BD Biosciences; San Jose, Calif.) was mobilized with HindIII and BamHI, and subcloned into the respective sites of pMFneo, and in turn, the expression cassette encompassing the EF1α promoter and the luciferase coding sequence was mobilized with NotI and subcloned into pSBC21.

For in vitro expression and purification of protein, a modified version of the LGFP expression plasmid was employed, pIRES2-EGFP (Clontech), into which was inserted sequentially a full Kozak sequence (GCCGCCACC) and an Igκ signal (leader) sequence (positioned upstream of a multiple cloning site, the internal ribosome entry site from encephalomyocarditis virus (ECMV), and GFP coding sequence). To this end, the AscI site and a 6× his coding sequence within the P8 oligonucleotide primer, and the XhoI site within the P4 and P7 primers were exploited. The subcloning placed the OX40·TRAIL or OX40·Fcγ1 coding sequences into the multiple cloning site of this vector, downstream and in-frame with the Igκ leader sequence, and upstream of the GFP reporter within the encoded bicistronic mRNA (to facilitate identification of cells producing recombinant protein). Plasmid DNA was propagated in *E. coli* and isolated endotoxin-free with a DNA isolation kit (Endofree Maxi Kit, Qiagen).

Bioluminescence Imaging:

Intradermal injection of naked DNA was performed in the dorsal right foot of each mouse, using a tuberculin syringe. Each mouse received 20 µg of DNA dissolved in 2×PBS, in a total volume of 20 µl. For CNS expression, mice received on day 8 post-challenge a single slow intrathecal injection into the cisterna magna, using a Hamilton syringe, of 3 µg of DNA in 9 µl of lipid (MLRI). The DNA:MLRI mixture was incubated at 37° C. for 30 min prior to injection. In the case of mice receiving luciferase expression constructs, imaging was performed 24 or 72 h later. Immediately after i.v. injection of 150 µg/kg body weight of D-luciferin in phosphate-buffered saline, mice were anesthetized with ketamine and xylazine (Sigma Aldrich). Imaging, using a cooled charge-coupled device camera (Xenogen, Hopkinton, Mass.) and a 1 min collection time, began 6 min after administration of D-luciferin.

Western Blotting:

20 µl aliquots of conditioned media generated from pOX40·TRAIL/SecTag or pOX40 Fcγ₁/SecTag stable transfectants were run on 12% acrylamide gels and transferred to nitrocellulose membranes. The membranes were directly probed with a peroxidase-conjugated polyclonal anti-human IgG Ab (Jackson ImmunoResearch, Inc.; 1:6,000). Blots were developed using Chemiluminescence Reagent Plus (PerkinElmer Life Sciences, Inc.). Membranes were then stripped of anti-IgG Ab using Western Blot Stripping Buffer (Pierce, Inc), and then probed with polyclonal rabbit anti-human OX40 Ab (Santa Cruz Biotechnology, Inc.; 1:5,000) as primary Ab, and peroxidase-conjugated polyclonal goat anti-rabbit Ab (Santa Cruz Biotechnology, Inc.; 1:10,000) as secondary Ab, and then developed as described above.

Contact Hypersensitivity:

Four week old female C57BL/6 mice, obtained from Jackson Laboratories, were sensitized subcutaneously with NP-O-Su (Biosearch Technologies, Inc) in DMSO as previously described (Yellayi et al., 2000 *Endocrine* 12: 207-213). Five days post-sensitization, intradermal injection of naked DNA was performed in the dorsal right foot using a tuberculin syringe. Each right foot received 20 µg of DNA dissolved in 2×PBS in a total volume of 20 µl, as described previously (Chesnoy S et al., 2002 *Mol Ther* 5: 57-62), while 2×PBS only was injected into the left foot. 24 h later, mice were re-sensitized in their right feet with NP-O-Su, while their left feet received only DMSO. Foot pad thickness was measured 24 h after re-sensitization, animals were sacrificed, and feet were then collected for sectioning and histopathological analysis. The difference in thickness between the right and left foot was analyzed. In this instance the thickness of the feet of naïve mice was used as the baseline.

To verify that suppression was local and not systemic, the right foot was injected with DNA and the left with 2×PBS only, and then both feet were challenged with antigen. In this instance, the difference in footpad thickness between the feet was determined.

Induction of EAE and intrathecal gene administration: Eight week old female C57BL/6 mice were immunized subcutaneously with 300 µg MOG peptide (38-50) in 200 µl of PBS:incomplete Freund's adjuvant 1:1 containing (2.5 mg/ml *Mycobacterium tuberculosis* H37RA, final concentration) divided over two injections of 100 µl each, one on either flank. Pertussis toxin (100 ng in 200 µl PBS) was administered i.p. immediately, as well as 48 h later. For treatment, animals were administered on day 8 post-challenge a single intrathecal injection (10 µl of the mixture slowly injected into the cisterna magna using a Hamilton syringe) of lipid-DNA complexes, containing 3 µg of DNA in 9 µl of lipid (MLRI), which was pre-incubated at 37° C. for 30 min before injection.

Mice were observed daily and assigned a clinical score based on the following scheme: 0, no clinical signs; 1, limp tail; 2, weak hind limbs; 3, paralyzed hind limbs; 4, weak forelimbs and paralyzed hind limbs; 5, moribund or dead. Mice with a score of 3 or greater were supplied with transgel (Charles River, Wilmington, Mass.) for hydration to prevent death from dehydration, along with chow on the floor of each mouse cage.

Histopathology:

Feet were fixed in neutral buffered formalin and decalcified for 24 hours before paraffin embedding. Brains and spinal cords were fixed in 10% phosphate-buffered saline overnight, and paraffin embedded. Sections (4 µm) were mounted on slides, dewaxed, rehydrated and stained with hematoxylin and eosin or luxol fast blue and cresyl violet, according to standard protocols.

Histopathological features in the spinal cord were assessed. Spinal cords were scored for demyelination, and the cellular components of inflammatory lesions in the sections were graded on a scale of 0-3. Demyelination in the sections was assessed using myelin-specific luxol fast blue staining of spinal cord white matter, with the following scoring: 0, no evident demyelination; 1, 0-10% white matter demyelinated; 2, 10-30% demyelinated, 3, >30% demyelinated. Monocyte and lymphocyte cells within the demyelinating lesions were identified by morphology in H&E-stained sections, and they were scored as follows: 0, no evident mononuclear cells; 1 <50 mononuclear cells per low power (10×) field; 2, 50-100 mononuclear cells per low power field; 3, >100 mononuclear cells per low power (10×) field. For the suppuration score, neutrophils within the demyelinating lesions were identified by morphology in H&E-stained sections, and they were scored as follows: 0, no neutrophil cells; 1 <5 neutrophils per low power (10×) field; 2, 5-10 neutrophils per low power field; 3, >10 neutrophils cells per low power field. The lesion score is an overall score obtained by summing the demyelination, monocyte/lymphocyte and suppuration scores.

The results of the experiments presented in this Example are now described.

Validation of the In Vivo Gene Transfer Approach Via Bioluminescence Imaging

As a first step, the feasibility of cutaneous gene transfer using the pND and SBC21 vectors, which incorporate the CMV and EF1α promoters, respectively, was established. Coding sequence for the luciferase reporter was inserted downstream of the respective promoters in the two expression vectors, generating pLuc/ND and pLuc/SBC21. 20 µg of the pLuc/ND expression construct was injected intradermally into the right feet of mice. Luciferase expression was readily detectable by bioluminescence imaging in the injected (right) feet for pLuc/ND (FIG. 1, right panel), with little decrement in expression at 72 h (when compared to 24 h post-injection; data not shown). Luciferase expression was not detected in any uninjected left feet (FIG. 1, right panel).

The ability of these luciferase reporter constructs to drive expression in the CNS was also evaluated. pLuc/ND and pLuc/SBC2 vector-liposome complexes were injected intrathecally, and strong CNS expression was reproducibly observed for both expression constructs at 72 h post-injection (FIG. 1, left and middle panels) and out to one week (data not shown).

OX40·TRAIL Decreases Local Contact Hypersensitivity

Figure 2A:
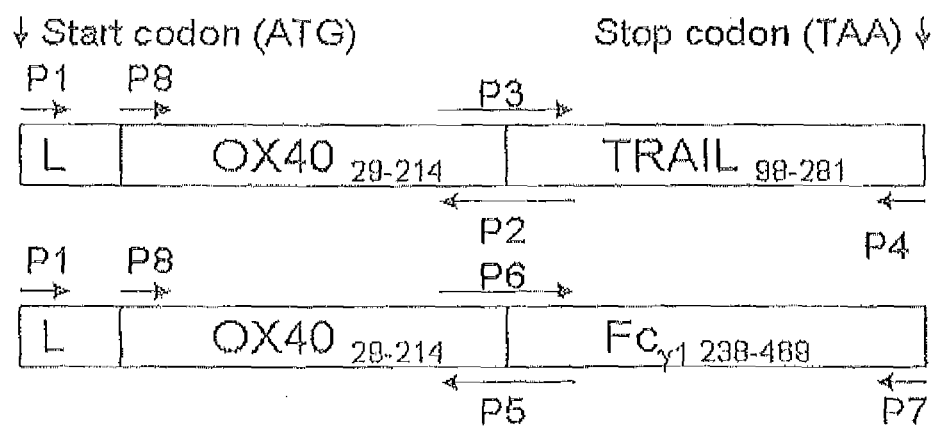
FIGS. 2A and 2B, is a series of images demonstration assembly and expression of chimeric proteins incorporating OX40.
Figure 2B:
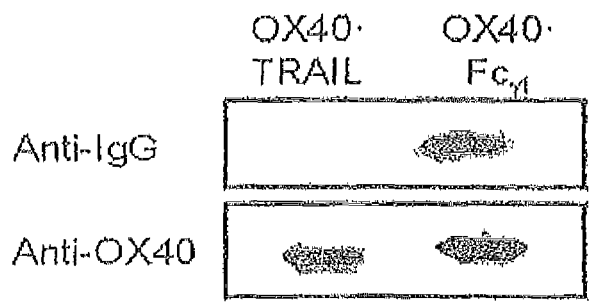

Having documented the utility of the pND and pSBC21 vectors for local (cutaneous and intrathecal) gene delivery using a luciferase reporter, the vectors were applied to local immunomodulatory protein expression. Towards this end, a novel TSCP, OX40·TRAIL (FIG. 2A, upper panel) was designed, in which the extracellular domain of OX40 (a Type I membrane protein) is linked to that of TRAIL (a Type II membrane protein). The chimeric coding sequence for this fusion protein, as well as a coding sequence for OX40-Fcγ$_1$ (FIG. 2A, lower panel) were subcloned into the expression vector pLGFP. In turn, the resulting pOX40·TRAIL/LGFP and pOX40. Fcγ$_1$/LGFP expression constructs were stably transfected into CHO-S cells. As shown in FIG. 2B, both encoded proteins could be readily detected in conditioned media from the transfectants, with the expected sizes (44 kD for OX40·TRAIL; 49 kD for OX40-Fcγ$_1$) verified on western blots of reducing denaturing gels.

Figure 3A:
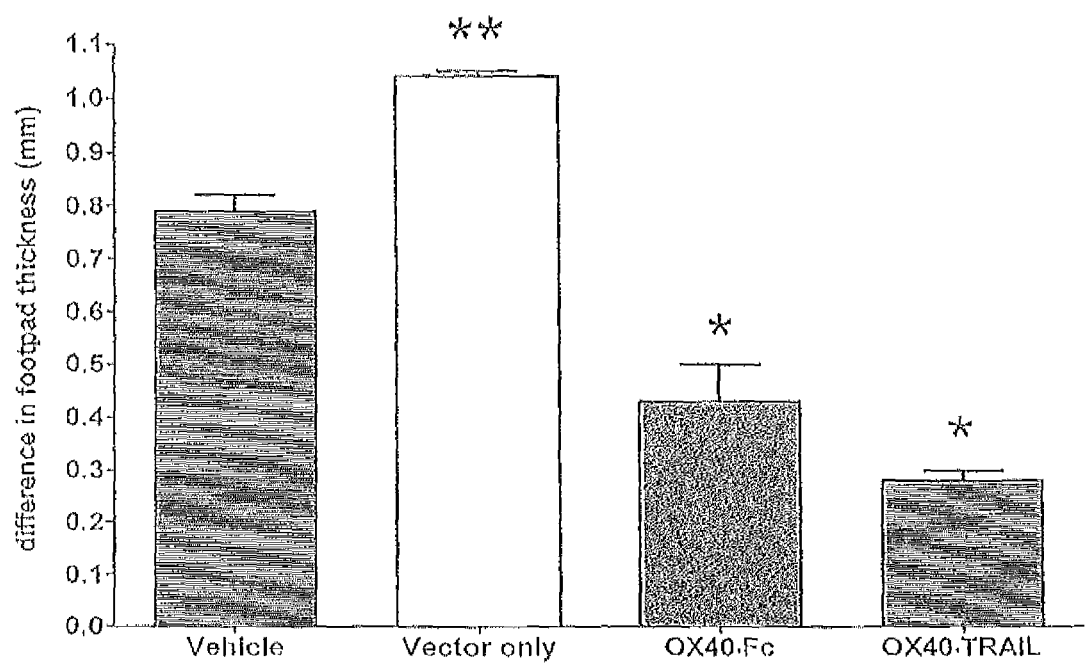
FIGS. 3A through 3C, is a series of images demonstrating inhibition of contact hypersensitivity by OX40·TRAIL and OX40·Fcγ1.
Figure 3B:
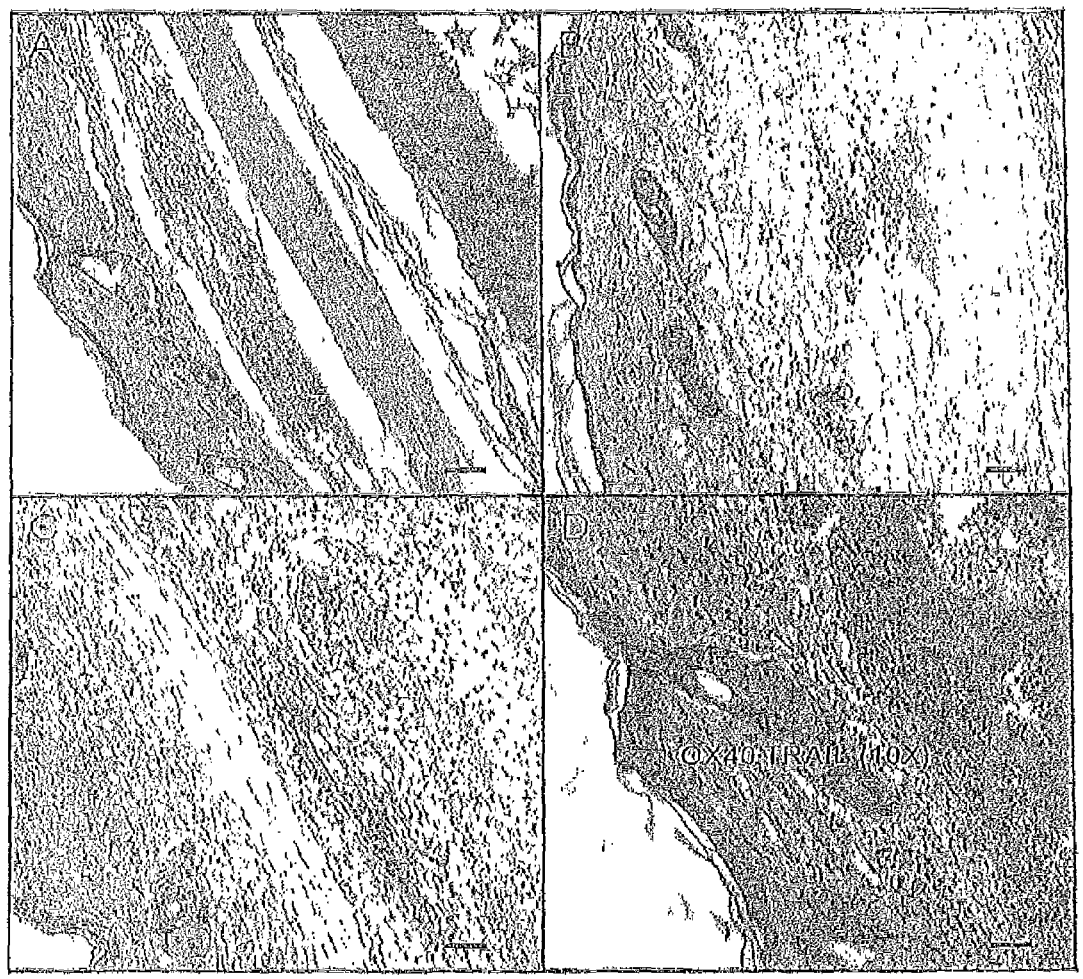

To permit in vivo expression, the same OX40·TRAIL and OX40·Fcγ$_1$ coding sequences were ligated into the expression cassette of pND, downstream of the CMV promoter, generating pOX40·TRAIL/ND and pOX40·Fcγ$_1$/ND, 20 µg of each was injected intradermally into the right footpads of mice 5 days after NP-O-Su sensitization. These feet were then resensitized with NP-O-Su 24 h after expression construct administration, and foot pad thickness was measured 24 h post-resensitization. Both OX40-containing expression constructs yielded significant ($p<0.05$) reductions in footpad thickness, compared to vector-only or no-vector control groups (FIG. 3A). Notably, histopathological evaluation revealed a significant reduction in edema of feet receiving the immunoinhibitory fusion proteins, notwithstanding persistent mononuclear infiltration (FIG. 3B). Inflammation was not seen in vehicle-injected, non-sensitized left feet.

Figure 3C:
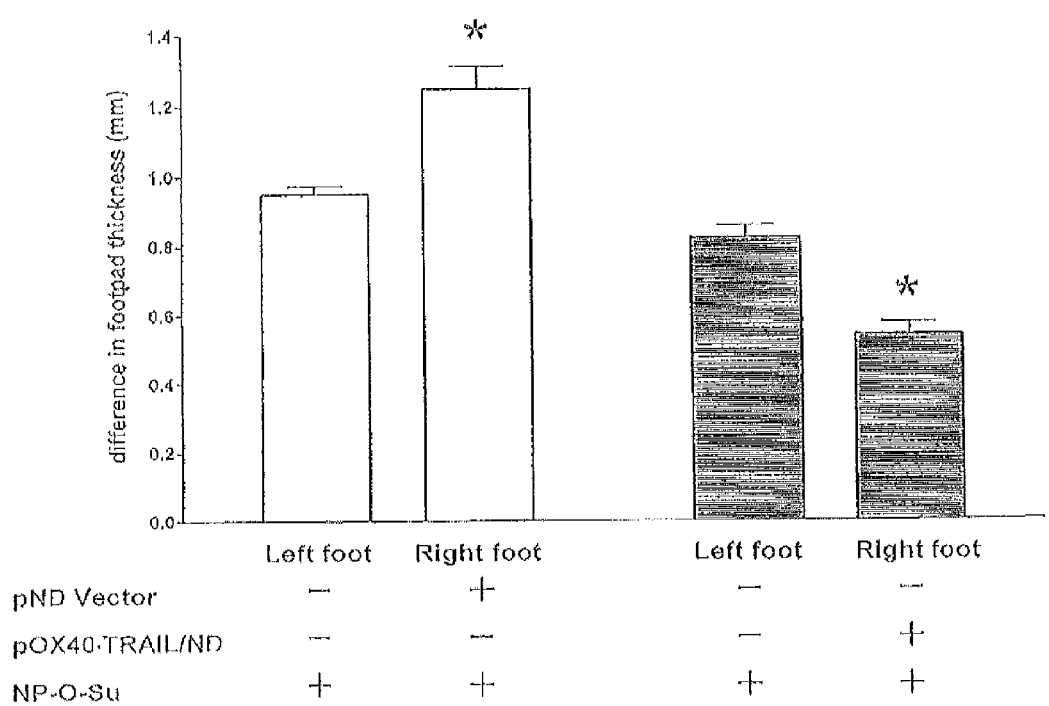

To determine if there is generalized immune suppression after cutaneous gene delivery, pOX40·TRAIL/ND (20 µg) was injected intradermally into right footpads 24 h prior to resensitization of both feet. Significant decreases in footpad thickness were evident only in plasmid-injected (right) feet (FIG. 3C), suggesting that immunosuppression is predominantly local and that there is no significant systemic effect of the cutaneously-expressed recombinant protein.

Figure 4A:
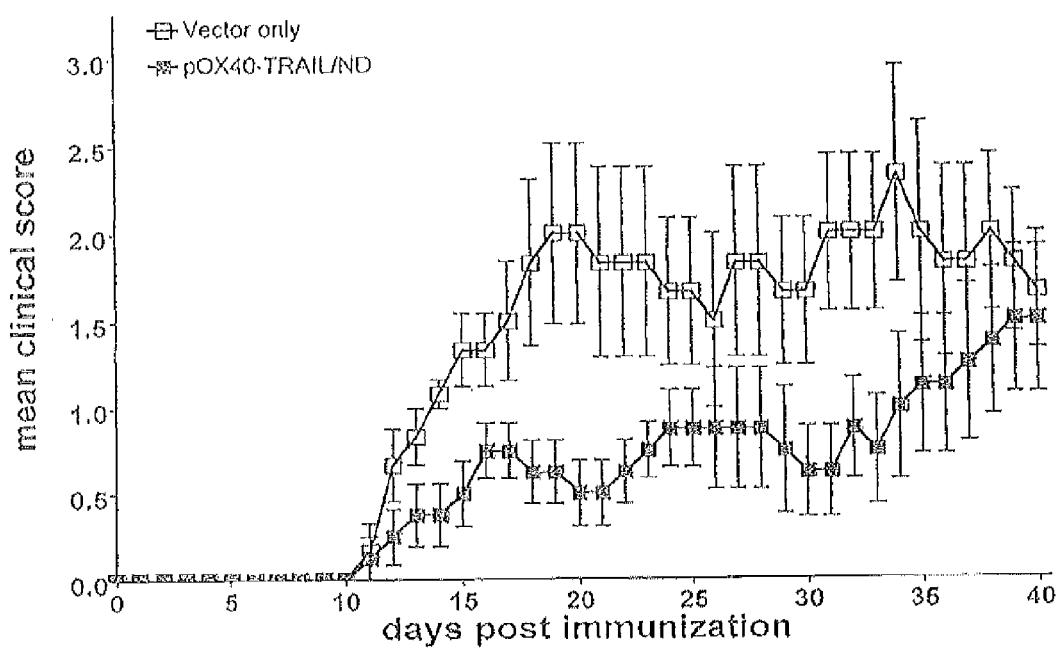
FIGS. 4A through 4D, is a series of images demonstrating suppression of EAE by intrathecal expression of OX40·TRAIL.
Figure 4B:
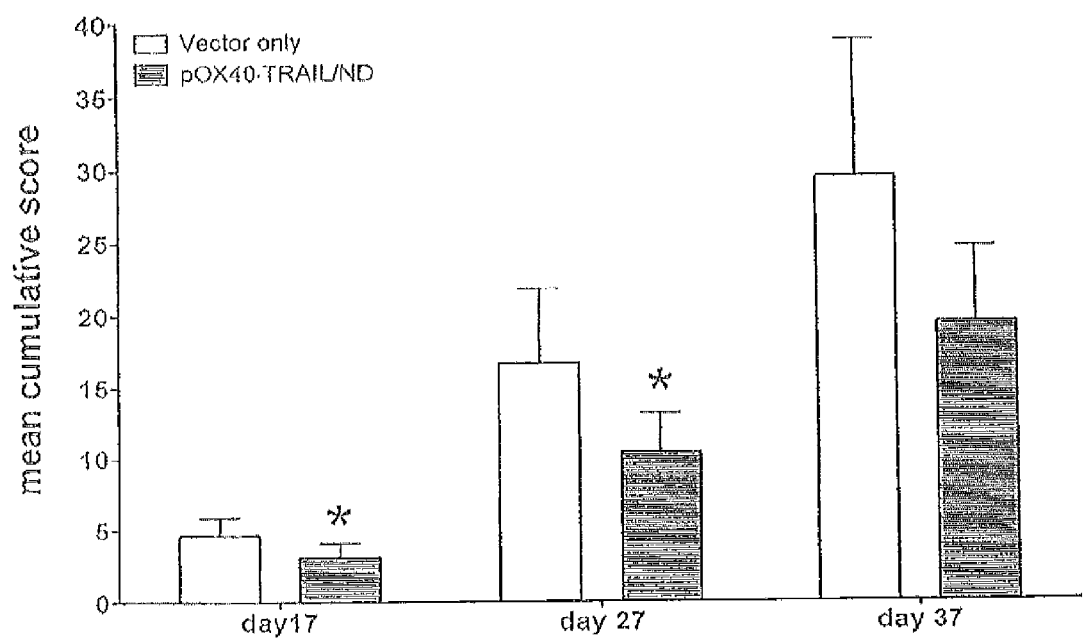

OX40·TRAIL Decreases EAE Severity More Effectively than its OX40 and TRAIL Components in Isolation Having validated the immunoinhibitory efficacy of OX40·TRAIL via cutaneous gene transfer in the classical contact hypersensitivity model, OX40·TRAIL's efficacy in another local gene delivery context, namely, intrathecal gene transfer in the setting of EAE, was evaluated. Specifically, mice were intrathecally injected 8 days post-MOG challenge with 3 µg of pOX40·TRAIL/ND versus pND plasmid vector only, complexed with 9 µl MLRI (in 10 µl total volume). As shown in FIGS. 4A and 4B, a single intrathecal injection of pOX40·TRAIL/ND significantly reduced the severity of EAE in the mice.

Figure 4C:
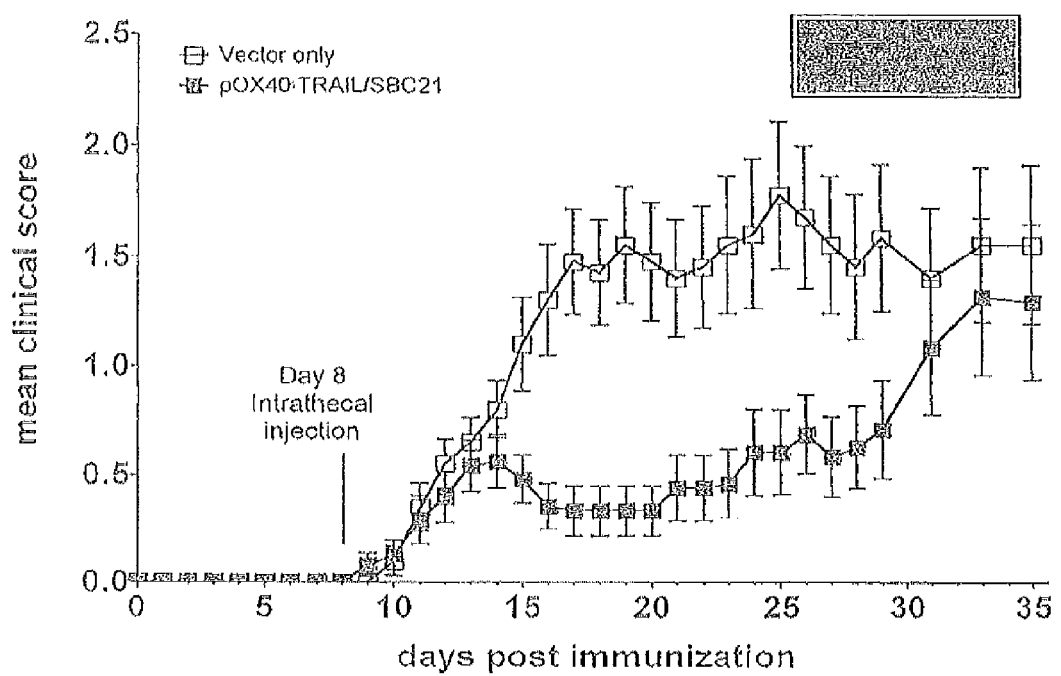
Figure 4D:
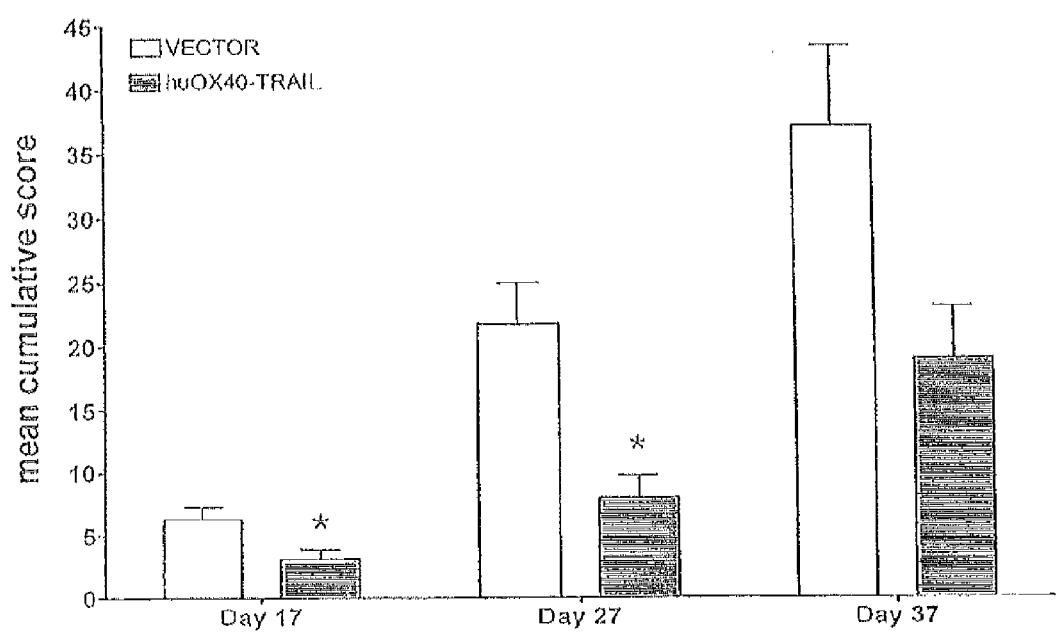

Even greater suppression was observed with the pSBC21 vector, which incorporates the EF1α promoter for gene expression (FIGS. 4C, 4D). Western blot analysis of the cerebrospinal fluid from animals receiving the pOX40·TRAIL/SBC21 expression construct showed readily detectable amounts of protein 10 days post-intrathecal injection (FIG. 4C, inset).

Figure 5A:
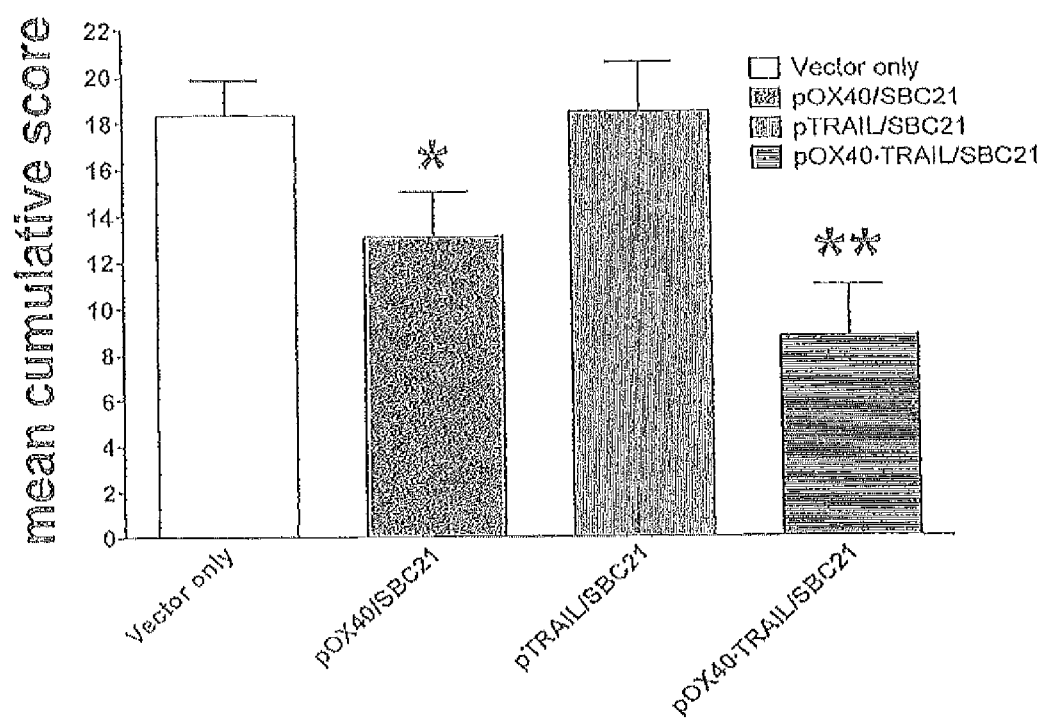
FIGS. 5A through 5C, is a series of images demonstrating enhanced suppressive function associated with OX40·TRAIL chimerization.
Figure 5B:
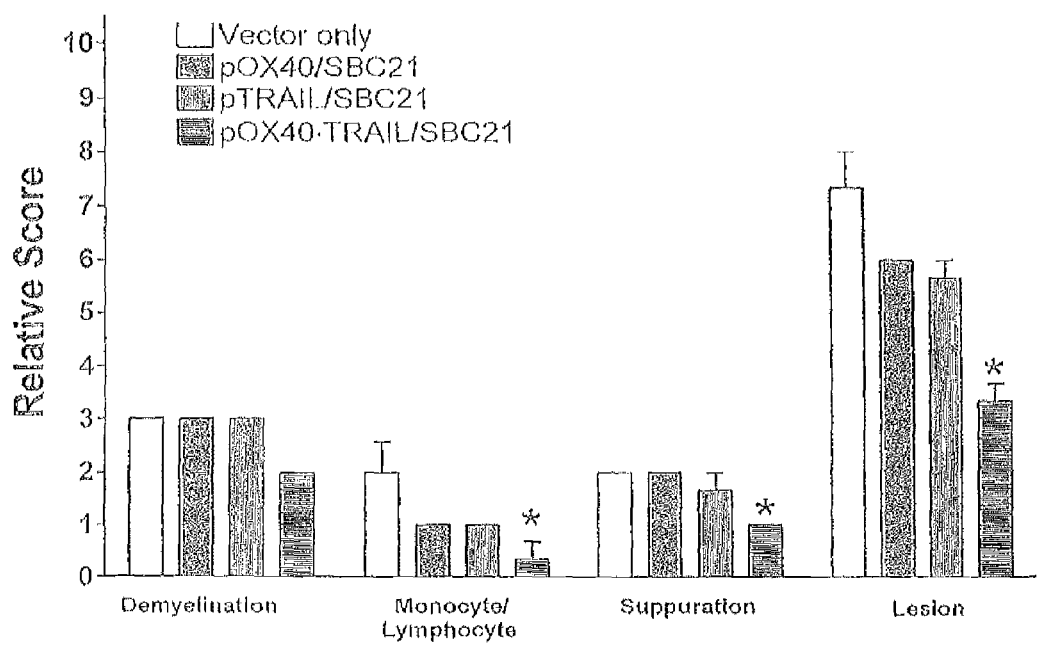

Another dimension was added to this analysis by comparing the function of the chimeric OX40·TRAIL protein with that of its component parts (OX40, TRAIL), each expressed in isolation. To this end, two additional expression constructs, pOX40/SBC21 and pTRAIL/SBC21, were constructed. Importantly, intrathecal administration of pOX40·TRAIL/SBC21 8 days post-MOG challenge (that is, before the onset of clinical signs of EAE) significantly decreased the EAE scores up to day 17, as compared to pOX40/SBC21, pTRAIL/SBC21, or pSBC21 vector-only treatment (FIGS. 5A, 5B). This finding of greater functionality of the fusion protein, compared to its component parts, parallels that for another fusion pair, CTLA-4·FasL (Huang and Tykocinski, 2001).

Histopathology in pOX40·TRAIL/SBC21-Treated Mice

Figure 5C:
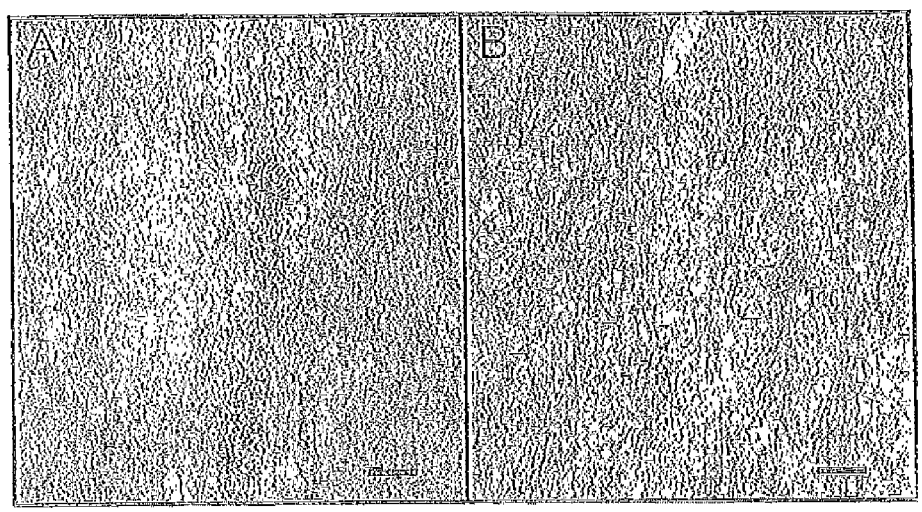

There were no significant differences in MOG-specific proliferation and cytokine production in lymphocytes from the periphery of OX40·TRAIL-treated mice (data not shown). The histopathological features of EAE model mice treated with OX40·TRAIL, or isolated component elements of the fusion protein were next examined. For this experiment, we selected mice from each group with a clinical score of 2.0-2.5 on day 17. The histopathological features of the brains and spinal cords were examined, and scores were assigned based on the histopathological features: demyelination, mononuclear cell infiltration, suppuration, and a composite score based on the sum of the other scores. Even for mice of the two groups with similar clinical scores and levels of demyelination, scores for the other histopathological feature differed significantly for OX40·TRAIL-treated mice. There was less severe suppurative leukomyelitis and perivascular lymphocytic infiltration in OX40·TRAIL-treated animals sacrificed on day 17, as compared to vector-treated mice (FIG. 5C). Furthermore, monocyte/lymphocyte infiltration, suppuration, and composite histopathological scores were significantly lower for pOX40·TRAIL/SBC21 treated animals, as compared to those treated with pOX40/SBC21 or pTRAIL/SBC21 (FIG. 5B).

FIG. 5C shows representative histological features of the demyelination and inflammation in OX40·TRAIL-treated mice compared to control mice. There was an equivalent degree of demyelination in the spinal cords from OX40·TRAIL– and vector only-treated mice. However, there was a pronounced decrease in the cellularity of the demyelinating lesions in the OX40·TRAIL-treated mice compared to the vector only-treated ones (FIGS. 5B and 5C). In particular, there was decreased monocyte/lymphocyte and granulocyte content in the demyelinating lesions of the OX40·TRAIL-treated group. These data suggest that there is a different outcome for lesion development in the OX40·TRAIL-treated mice compared to mice which did not receive OX40·TRAIL.

The decrease in monocyte/lymphocyte score and the decrease in granulocyte numbers in the OX40·TRAIL-treated mice suggests that OX40·TRAIL has differential effects on the various cellular components of the CNS-infiltrating cells.

Whereas particular embodiments of this invention have been described above for purposes of illustration, it will be evident to those skilled in the art that numerous variations of the details of the present invention may be made without departing from the invention as defined in the appended claims.

What is claimed:

1. A fusion protein comprising a first domain and a second domain, wherein the first domain consists of a portion of the extracellular domain of an OX40 protein that binds OX40 ligand and interferes with its ability to bind and trigger a membrane-bound OX40 receptor and the second domain consists of a TRAIL protein that binds to a TRAIL receptor and directs inhibitory signals through the receptor.

2. The fusion protein of claim 1, wherein the fusion protein is SEQ ID NO: 1 or SEQ ID NO: 2.

3. A fusion protein comprising a sequence selected from the group consisting of SEQ ID NO: 1 and SEQ ID NO: 2.

4. The fusion protein of claim 1, wherein the first domain is human OX40 and the second domain is human TRAIL.

5. The fusion protein of claim 1, in a pharmaceutically acceptable carrier.

6. A pharmaceutical composition comprising the fusion protein of claim 1.

7. A method of treating or ameliorating an autoimmune disease in a patient comprising administering the fusion protein of claim 5 or claim 6 to a patient in need of such treatment.

8. The method of claim 7, wherein the autoimmune disease is multiple sclerosis.

9. The method of claim 7, wherein administration is parenteral.

10. A method of treating or ameliorating an alloimmune disease in a patient comprising administering the fusion protein of claim 5 or claim 6 to a patient in need of such treatment.

11. A method of treating or ameliorating cancer in a patient comprising administering the fusion protein of claim 5 or claim 6 to a patient in need of such treatment.

* * * * *